United States Patent [19]

Scharf et al.

[11] Patent Number: 4,681,046
[45] Date of Patent: Jul. 21, 1987

[54] METHOD OF UTILIZING DISTILLATION RESIDUES OF PHTHALIC ACID ANHYDRIDE OR MALEIC ACID ANHYDRIDE

[75] Inventors: Helmut Scharf, Schermbeck; Wilfried Krix, Bottrop, both of Fed. Rep. of Germany

[73] Assignee: Huls Aktiengesellschaft, Marl, Fed. Rep. of Germany

[21] Appl. No.: 873,549

[22] Filed: Jun. 12, 1986

[30] Foreign Application Priority Data

Jul. 12, 1985 [DE] Fed. Rep. of Germany ....... 3524919

[51] Int. Cl.$^4$ .............................................. F23G 5/02
[52] U.S. Cl. .................................... 110/346; 110/222; 110/229
[58] Field of Search ............... 110/222, 229, 232, 347, 110/346; 48/197 R

[56] References Cited

U.S. PATENT DOCUMENTS 4,557,204 12/1985 Faehnle ................................. 110/346
4,630,556 12/1986 Scheffee ........................... 110/222 X Primary Examiner—Edward G. Favors
Attorney, Agent, or Firm—Oblon, Fisher, Spivak, McClelland & Maier

[57] ABSTRACT

A method for utilizing distillation residues of phthalic anhydride or maleic anhydride, which comprises: (a) cooling hot, liquid distillation residues of said phthalic anhydride or maleic anhydride while flowing as a stream in a first organic liquid; (b) comminuting said distillation residues solidifying in said first organic liquid by means of a cutting edge rotating at high rpm to produce a granulate; (c) suspending said granulate in a second organic liquid; and (d) incinerating the suspension or converting the suspension into synthesis gas.

11 Claims, 3 Drawing Figures

METHOD OF UTILIZING DISTILLATION RESIDUES OF PHTHALIC ACID ANHYDRIDE OR MALEIC ACID ANHYDRIDE

BACKGROUND OF THE INVENTION

1. Field of the Invention

The present invention is directed to a method of utilizing distillation residues of phtalic acid anhydride or maleic acid anhydride.

2. Description of the Related Art

Phthalic anhydride (PA) is produced industrially by oxidation of o-xylene or naphthalene with air, in the gas phase. The PA produced in this process must be distilled in order to satisfy high purity requirements placed upon it. The distillation produces a residue which is a liquid at temperatures above c. 180° C., and which yields a mass which is viscous to glassy when cooled.

Two methods of disposing of this residue are used industrially. In one such method, the distillation is carried out only to the point where the residue contains 50 wt. % PA. At high temperatures, the residue has relatively low viscosity, so that it can be pumped. It is fed to appropriate incineration devices and is incinerated. In order to maintain the residue in a state in which it can be readily conveyed, valuable products are left in the residue. Therefore, when the residue is incinerated, the valuable products are incinerated as well. This is a disadvantage of the first method.

In the second method, the PA is distilled off to the point where the residue is just barely capable of being removed from the distillation apparatus. During this removal, PA escapes, and can lead to contamination of the apparatus. The residue is cooled off in tank, and then must be broken up and transported to the incineration equipment. This processing is cumbersome and expensive.

A distillation residue is also produced in the manufacture of maleic anhydride (MA). Heretofore, this residue has been dissolved in water and discharged as waste water, which represented a substantial burden on the environment.

In view of the disadvantages of prior methods of treating the distillation residues of phthalic acid anhydride or maleic acid anhydride, a need continues to exist for new methods of processing these residues.

SUMMARY OF THE INVENTION

Accordingly, an object of the invention is to provide a method which makes the processing of distillation residues simpler and more secure, does not burden the environment, and adds value to the residues.

This object, among others, has been achieved by providing a method in which the hot, liquid distillation residue flows as a stream into a cooled organic liquid in which a cutting edge is moved at a high rate of revolution. During cooling and hardening, the residue is sliced by the cutting edge, whereby granules collect on the bottom of the vessel, and these granules are ground along with the organic liquid to form a readily pumpable suspension which can be used as a fuel to produce steam, or can be used to produce synthesis gas.

BRIEF DESCRIPTION OF THE DRAWINGS

A more complete appreciation of the invention and many of the attendant advantages thereof will be readily obtained as the invention becomes better understood by reference to the following detailed description when considered in connection with the accompanying drawings, wherein.

DESCRIPTION OF THE PREFERRED EMBODIMENTS

Figure 1:
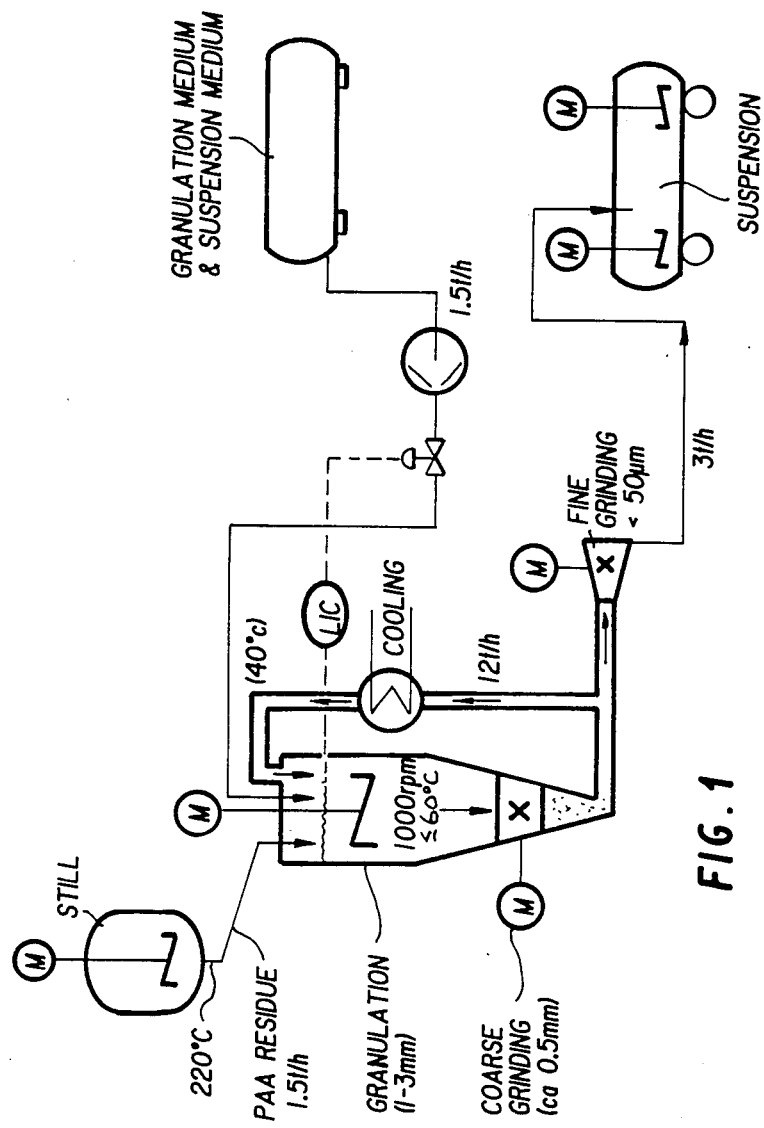
FIG. 1 is a scheme for suspension of PA distillation residue, with integrated granulation and coarse grinding.
Figure 2:
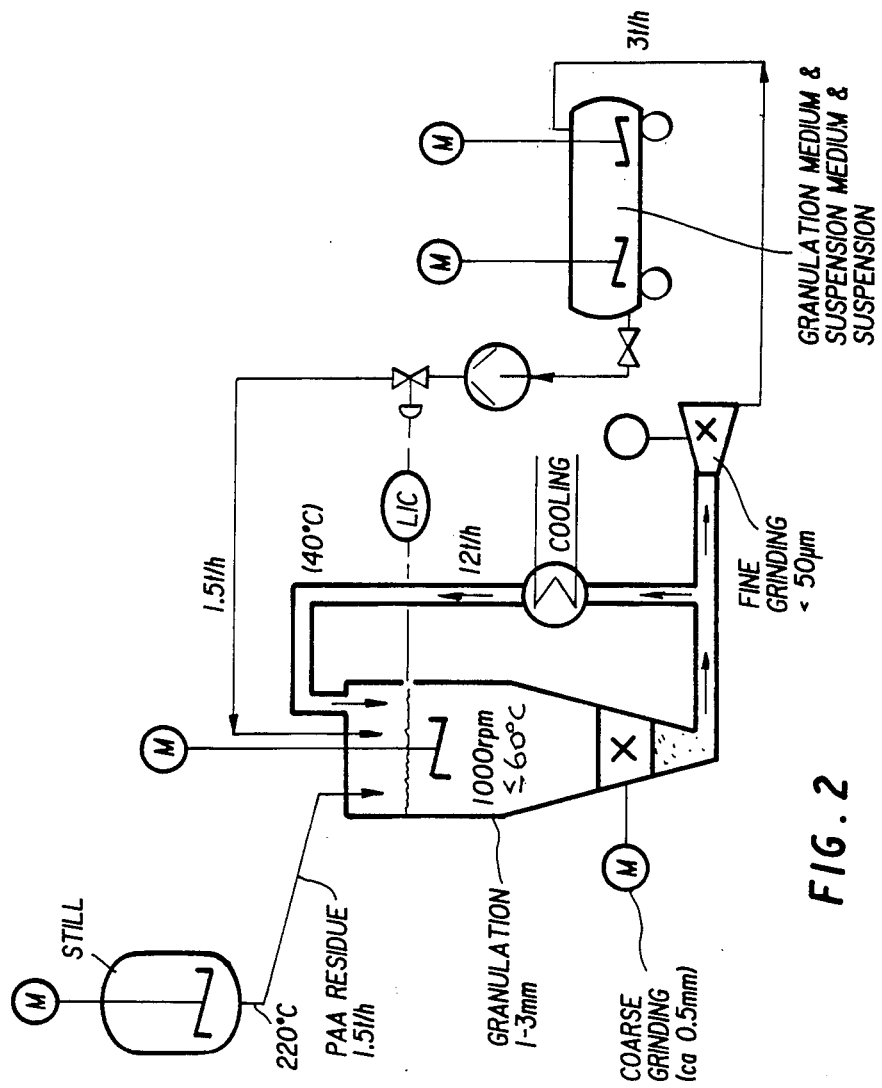
FIG. 2 is a scheme for suspension of PA distillation residue with integrated granulation, coarse grinding, and fine grinding.
Figure 3:
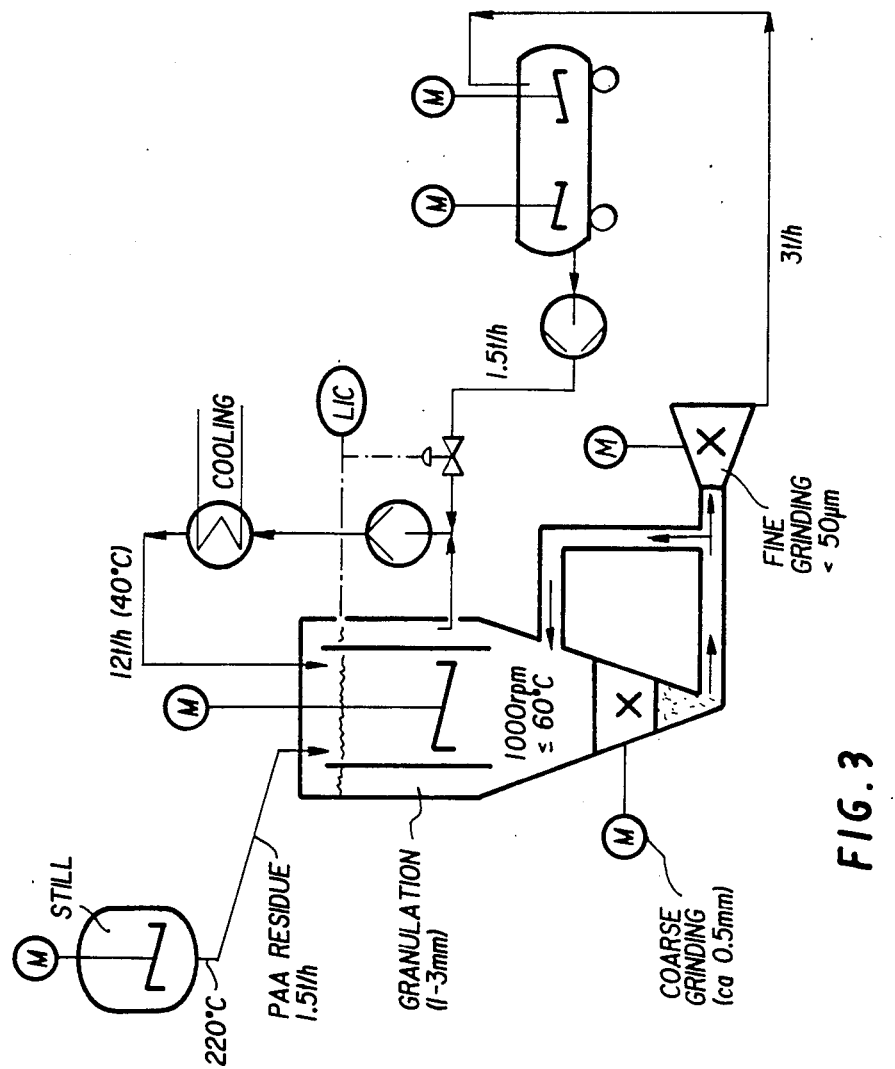
FIG. 3 is a scheme for suspension of PA distillation residue with integrated granulation and fine grinding.

The inventive method has the advantage that the residue from the PA distillation is transformed into a form which is easily handled at room temperature, thereby substantially simplifying further processing. Since the method, when used for PA residue processing, is preferably employed for PA residues which have been thorougly distilled, substantial additional amounts of PA are recovered in comparison with known methods, so that the unit costs of the PA distillation are reduced. When the inventive method is used in MA production, the production of waste waters is avoided, so that the burden on the environment is eliminated. Further, the residues may not only be burned in combination with a steam production process, but alternatively they may be converted to synthesis gas, depending on the suspension medium employed. Accordingly, substantial economic benefits are possible.

The chemical structure of the PA residue coming from the distillation apparatus is not precisely known; it may have widely varying properties. Depending on the temperature, which is generally between 200° and 250° C., and further depending on the degree of distillation and particularly on the starting material (o-xylene or naphthalene), it may be anywhere from a thin liquid to a highly viscous material.

The chemical composition of the MA residues is not precisely known, and the external appearance and physical state of the MA residue also depends on the starting material of the MA manufacturing process (benzene or 4-C hydrocarbons) and the degree of distillation. Depending on the temperature, which is generally between 170° and 180° C., and the content of fumaric acid, the MA residue may be anywhere from a thin liquid to a pasty mass.

Candidates for suspension media are organic substances which are liquid at room temperature. Since as a rule these are burned along with the PA and MA residues, or are converted into synthesis gas along with the residues, they should contain little or no halogen, sulfur, or nitrogen. On the other hand, oxygencontaining compounds are suitable. The preferred suspension media are aliphatic or aromatic hydrocarbons, e.g. paraffin oil and light heating oil. Particularly preferred are liquid organic wastes from other production processes, e.g. distillation residues from alkylation units (such as residues of ethylbenzene and its derivative styrene, residues of cumene, and residues of relatively longchain paraffins; with these possibly occurring in mixtures with aromatics from the Tensid process), and distillation residues from alcohol manufacture (such as distillation residues of n-butanol, iso-butanol, and 2-ethylhexanol). Due to the large number of possible suspension media, experimental tests must be carried out in individual cases to determine whether the material is suitable for granulation and suspension of the PA and MA residues.

The details of the cooling and granulation of the PA and MA residues depend on the properties of the residues and of the suspension medium. Because the residues can differ substantially in their outward characteristics, and because a relatively large number of suspension media is available, experiments must be carried out in individual cases to determine whether the particle size distribution is suitable for the subsequent suspension. Therefore, the following data can serve only as guideline values. The processing according to the inventive method for the PA and MA residues is not essentially different for the respective residues. Accordingly, for the sake of simplicity, the method will be described hereinafter only for the PA residue.

The PA residue flows freely under gravity into the suspension medium. Under these conditions, the diameter of the stream may vary between around 1 and 10 cm, depending on the desired flow rate and the outward properties of the PA residue. The stream diameter is generally 2-5 cm. The length of the cooling segment, i.e. the height of the liquid column, must be chosen such that after passing through this segment the granulate has hardened to the extent that it can be ground in the presence of the cooling medium (which cooling medium is generally also the suspension medium). The length of the cooling segment, in addition to depending on the characteristics and amount of the PA residue stream, depends chiefly on the temperature of the cooling medium and the rpm of the cutting edge rotating in the cooling medium. For a very fine stream of PA residue (0.5 cm, for example), a liquid column of around 30 cm is sufficient for the cooling segment. With stream diameters which are typical in the art (2-5 cm), the height of the liquid column is about 80-120 cm. The determining factor for the amount of cooling liquid is the mixture temperature which develops after the cooling of the PA residue.

The lower limit of the mixture temperature is imposed by the viscosity increase of the cooling medium with decreasing temperature. Because the minimum viscosity is desirable for further processing of the granulate, and the simplest situation is to be able to handle the mixture at room temperature, and since it is quite costly to cool the mixture to less than room temperature, the preferred lower bound of the temperature is ambient temperature. The upper limit of the mixture temperature depends on the characteristics of the PA residue, but it also particularly depends on the type of cooling medium employed. To the extent possible, the cooling medium should be chosen such that it does not dissolve the PA residue, or dissolves it to a very small extent. As a rule, this temperature will be 60°-90° C. At higher temperatures, the specific dissolving properties of the cooling medium become increasingly involved. Thus, for example, a PA residue can be converted, with a mixture of styrene, ethylbenzene, and cumene distillation residues at 120°-130° C., into a solution-emulsion which is pumpable at these temperatures but which upon cooling hardens to a tarry and essentially unmanageable mass.

From a process engineering standpoint, the amount of cooling liquid depends on whether the PA distillation is carried out continuously or discontinuously, further on the amounts of PA residue to be granulated per unit time, on the temperatures of the PA residue and the cooling medium, and on whether the cooling medium is passed in a loop through an external cooling device.

The rotating cutting edge in the liquid has two functions. First, it serves to cut up the solidifying PA stream, and secondly it must bring about rotation of the cooling liquid to such a degree that good heat transfer results for cooling the PA residue stream. On the other hand, the area of the cutting edge perpendicular to the direction of rotation must not be too great, because otherwise PA residue which has not yet completely hardened may come against the surface of the cutting edge and harden at that location, which will lead to the formation of lumps in the PA residue.

In the simplest case, the cutting edge will comprise a narrow, flat steel implement. However, it may also comprise a multi-vaned propeller. Because the flat steel implement fulfills the requirements in the simplest manner, it is preferred as a rule.

The adjustment of the cutting edge in the column of liquid depends on the thickness, the descending speed, and the hardening time of the PA residue stream. As a rule, the height of the liquid column over the cutting edge is c. 10-50 cm.

The rpm rate of the cutting edge may vary over a very wide range. It also depends on the characteristics of the PA residue stream and the characteristics of the cooling medium, particularly the viscosity. In addition, the rpm depends on the desired granule size of the granulate. The higher the rpm, the finer the granulate. Thus, for example, in paraffinic hydrocarbons or in light heating oil at 600 rpm, a particle size range of c. 5-25 mm is produced. At 1,000 rpm in the same cooling media, the particle size is only c. 1 mm for paraffinic hydrocarbons and c. 1-3 mm for light heating oil. Because a fine particle size is more advantageous for further processing, generally revolution rates of c. 1,000 to 3,000 rpm are preferred.

The cooling energy for cooling the PA residue is provided by pumping the cooling liquid over a cooling segment, which segment may be disposed inside or outside of the granulation vessel. Because additional heat is produced in the subsequent grinding step, external cooling is preferred in combination with the grinding. The ratio of PA residue to circulated cooling medium must be set such that the maximum permissible mixing temperature (as a rule, 60°-90° C.) is not exceeded. Thus, assuming that the heat capacity of the cooling medium is comparable to that of the PA residue, 8 tons of cooling medium per hour are required to cool 1 ton of PA residue per hour from 220° C. to 60° C., if the cooling segment for the cooling medium is designed to cool circulated cooling medium from 60° C. to 40° C.

The PA residue produced in the inventive granulation can be separated from the cooling medium and burned separately, or, according to the invention, it may be further processed along with the cooling medium to yield a pumpable suspension. Another possibility is to employ different liquids for the cooling and the suspension. This latter may be a practical option on economic grounds, if there is a substantial distance between the production of the residue and the location of the further processing; it may also be advantageous if for ecological reasons it is undesirable to transport the suspension medium. The inventive production of a suspension based on the granulate is carried out generally with means and apparatus known in the art, e.g. colloid mills. The granulate may be fine-ground in the presence of the cooling medium (which medium according to the invention serves simultaneously as the suspension medium) in one or two steps, and in a single pass or with recycle, depending on the particle size distribution of the granulate, the desired final particle size range in the suspension, and the desired throughput.

The fineness of the particle size in the suspension depends on the desired stability of the suspension. If the suspension is to be immediately further processed or is to be permanently stirred, then the particle size does not need to be as fine as it does if there is a need for the suspension to be storage-stable for some appreciable time. The desired particle size also depends on the type of suspension medium. Thus, when using a suspension medium comprising distillation residues of styrene, ethylbenzene, and cumene, a particle fineness of 20–150 microns is sufficient to yield a suspension stable for several days, but for a suspension in light heating oil, the particle size should be in the range of c. 10–50 microns. As a rule, particle sizes below 50 microns are preferred.

The ratio of PA residue to suspension medium depends mainly on the apparatus which may be used for further processing of the suspension. For reasons of economy, one strives for the highest possible content of PA residue in the suspension. The viscosity of the suspension increases sharply with increasing content of PA residue, so that problems can arise when the suspension is fed to a synthesis gas apparatus—problems relating to the high pressure pumps and the valves. As a rule, the ratio of PA residue to suspension medium is 1:1 to 2:1. Depending on the suspension medium, the viscosity of the suspension is up to c. 1,500 mPa-sec.

The fine grinding and the establishment of the suspension mixture ratio may take place in a single step, with the granulate being conveyed from the granulator into the colloid mill with the aid of a screw conveyor. Often, the liquid disposed in the granulate interstices is sufficient to provide a mixture ratio of c. 1:1 by weight. In the case of a granulate which is very coarse, it is advisable to carry out the grinding in two stages, in order to increase the processing rate of the PA residue. For example, the particle size may be reduced from 3 mm to 0.5 mm in the first grinding stage, and from 0.5 mm to <50 microns in the second grinding stage. With the PA residue fed in a single pass through the granulation and the coarse and fine grinding, the cooling medium must be sent throuth an external cooling loop at the granulation stage, or else the cooling device must be present in the granulating vessel, with the cooling liquid being vigorously stirred. A preferred embodiment of the inventive method comprises combining cooling and granulation with the coarse grinding. In this arrangement, the mixture exiting from the coarse grinding stage is recycled through a cooling unit and into the granulation vessel, with the grinder serving simultaneously as a conveying pump. Product from the coarse grinding is drawn off in a side stream and sent to a fine grinder and then to a storage container or to the synthesis gas unit. As a rule, the amount of PA residue to be processed is determined, then an equal amount of fresh cooling medium is added in the granulation vessel, and most of the product from coarse grinding is passed to the recycle loop, while a minor part, corresponding to the amount of PA residue plus the amount of fresh cooling medium, is drawn off through the fine grinder as the finished suspension (with the ratio of PA residue to suspension medium being 1:1), for further processing.

In another embodiment of the inventive method, the finished suspension is pumped into the storage container for the cooling medium and is subjected to granulation along with the cooling medium (which is the suspension medium).

According to the invention, the method described is also applicable to the processing of distillation residues of maleic anhydride (MA). Further, in general, the method is applicable to organic materials which are liquid at relatively high temperatures and are solid and grindable at room temperature.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A method for utilizing distillation residues of phthalic anhydride or maleic anhydride, which comprises:
   (a) cooling hot, liquid distllation residues of said phthalic anhydride or maleic anhydride, while flowing as a stream in a first organic liquid;
   (b) comminuting said distillation residues solidifying in said first organic liquid by means of a cutting edge rotating at high rpm to produce a granulate;
   (c) suspending said granulate in a second organic liquid; and
   (d) incinerating the suspension or converting the suspension into synthesis gas.

2. A method according to claim 1, wherein said first and second organic liguids are a single organic liquid.

3. A method according to claim 1, wherein said first or second organic liquid comprises distillation residues from other manufacturing processes.

4. A method according to claim 2, wherein said single organic liquid comprises distillation residues from other manufacturing processes.

5. A method according to claim 1, wherein said first or second organic liquid comprises light heating oil.

6. A method according to claim 2, wherein said single organic liquid comprises light heating oil.

7. A method according to claim 1, wherein said cooling liquid is passed through a recycle loop including a cooling unit.

8. A method according to claim 1, wherein part of the cooling liquid along with coarsely ground granulate or part of the finished suspension is recycled, via a path including a cooling unit, to a cooling stage in which the stream of hot distillation residue is solidified.

9. A method according to claim 1, wherein said comminuting comprises a coarse grinding stage and a fine grinding stage.

10. A method according to claim 1, wherein said cutting edge is rotated at from about 1,000 to 3,000 rpm.

11. A method according to claim 1, wherein said cutting edge is a flat steel implement.

* * * * *